«12» United States Patent
Sardo

(10) Patent No.: US 8,207,090 B2
(45) Date of Patent: Jun. 26, 2012

(54) PROCESS FOR THE ANTI-GERMINATION AND/OR BIOCIDE TREATMENT OF BULBS OR TUBERS BY MEANS OF CIPC AND A TERPENE OR TERPENE OIL

(75) Inventor: Alberto Sardo, Chateaurenard (FR)

(73) Assignee: Xeda International, Saint-Andiol (FR)

( * ) Notice: Subject to any disclaimer, the term of this patent is extended or adjusted under 35 U.S.C. 154(b) by 588 days.

(21) Appl. No.: 11/150,225

(22) Filed: Jun. 13, 2005

(65) Prior Publication Data

US 2006/0276336 A1 Dec. 7, 2006

(30) Foreign Application Priority Data

Jun. 2, 2005 (FR) ...................................... 05 05600

(51) Int. Cl.
*A01N 25/00* (2006.01)
(52) U.S. Cl. .................................................. 504/116.1
(58) Field of Classification Search ................ 504/116.1
See application file for complete search history.

(56) References Cited

U.S. PATENT DOCUMENTS

| 5,622,912 | A  | * | 4/1997 | Riggle et al. ................... | 504/143 |
| 5,811,372 | A  | * | 9/1998 | Riggle et al. ................... | 504/138 |
| 6,723,364 | B1 | * | 4/2004 | Bompeix et al. .............. | 426/320 |
| 2007/0027033 | A1 | * | 2/2007 | Sardo ............................ | 504/348 |

OTHER PUBLICATIONS

Kleinkopf et al., Sprout inhibition in storage: Current Status, New Chemistries and Natural Compounds, American Journal of Potato Research 8:317-327, 2003.*
Kleinkopf et al., Alternative Sprout suppressants for stored potatoes, Idaho Potato Conference, 2002.*
Potato Varieties: A Comprehensive List, Washington State University, <http://potatoes.wsu.edu/varieties/vars-all.htm> 2009.*

* cited by examiner

*Primary Examiner* — James H Alstrum Acevedo
*Assistant Examiner* — Thor Nielsen
(74) *Attorney, Agent, or Firm* — B. Aaron Schulman, Esq.; Stites & Harbison, PLLC

(57) ABSTRACT

A process for the anti-germination and/or biocide treatment of bulbs or tubers by separate application of 3-chlorophenyl-isopropylcarbamate (CIPC) and a component selected from the group consisting of clove oil and eugenol, in this order or vice versa. The process may be used for the treatment of potato tubers.

15 Claims, No Drawings

PROCESS FOR THE ANTI-GERMINATION AND/OR BIOCIDE TREATMENT OF BULBS OR TUBERS BY MEANS OF CIPC AND A TERPENE OR TERPENE OIL

TECHNICAL FIELD

The present invention relates to a process for the anti-germination and/or biocide treatment of bulbs and tubers by means of CIPC and one or more terpenes or terpene oils. This process is particularly suitable for the treatment of potato tubers.

BACKGROUND TO THE INVENTION

After harvesting of potatoes or other tubers, said tubers are preserved at temperatures of approximately 20 to 30° C. for about 10 days in order to harden their peridermal layer (or "skin"), then gradually cooled to their preservation temperature, which is about 10° C.

During the first and second months following their harvest, the tubers remain in the rest state and exhibit few germination tendencies.

Nevertheless, before the end of this period, the tubers have to be chemically treated in order to inhibit germination, which would cause detrimental effects, such as loss in weight, preservation of the sugar starch, a decrease in the quality of the tubers and deterioration of their appearance. Furthermore, the sprouts and the surrounding tissues contain high levels of toxic glycoalkaloids, which are not destroyed during cooking.

The most commonly used anti-germination treatment processes employ chemical agents such as chloropropham, CIPC or 3-chlorophenylisopropylcarbamate. Generally, CIPC is applied to stored tubers using thermal fogging processes.

Generally, thermal fogging involves the application of CIPC by means of a hot air stream in order to produce an aerosol.

According to a first practice, the thermal fogging is carried out using pure CIPC. However, this process results in an unsatisfactory manner in the application of the pure active ingredient on the tubers. This is because the CIPC tends to form crystals and/or is not distributed uniformly on the tubers.

According to another practice, the CIPC is formulated in a solvent medium, such as methylene chloride or methyl alcohol. In this case, too, this process does not provide satisfactory results in so far as the solvents that are conventionally used have low boiling points and tend to evaporate rapidly during the thermal fogging. This results in the application of pure active ingredient having the same drawbacks as the preceding process.

Furthermore, CIPC dissolves with difficulty in conventional solvents, and maximum CIPC concentrations of approximately 30% (weight/volume) are generally obtained. At best, concentrations of approximately 54% at 180° C. have been obtained. This low solubility entails the use of large amounts of solvent and/or formulation in order to obtain the required amounts of active ingredient. Nevertheless, efforts are generally made to limit the use of these solvents owing to their inherent toxicity and/or the danger of use that they entail, especially as a result of their low boiling points, which result in high risks of flammability.

The use of synthetic derivatives for application to fruits and vegetables during growth or storage thereof is limited. CIPC levels, in particular are subject to increasingly stringent regulations. Accordingly, although CIPC is used to limit the formation of sprouts on the tubers, its toxicity might call into question its use at conventional application rates. It is accordingly desirable to limit as far as possible the amount of CIPC to be applied to bulbs and tubers.

Finally, available CIPC formulations exhibit poor stability, especially at low temperature, and this means that they are unsuitable for storage, especially in the cold stores for storing bulbs and/or tubers.

Attempts have been made to apply CIPC with terpene compounds in order to inhibit potato sprouts; more precisely. U.S. Pat. No. 5,811,372 relates to a method for the inhibition of tuber sprouts involving the application of CIPC and carvone. Nevertheless, the two agents are mixed in the composition to be applied. Furthermore, the same patent specifies that the combination of CIPC with similar derivatives (limonene or jasmone) does not produce positive results. Moreover, there is no indication of the effect of the carvone on the applicability and the distribution of the CIPC. Finally, there is no reference to the CIPC concentration levels being higher than those of the terpene.

It has now been discovered, and this is one of the subjects of the present invention, that terpenes and/or terpene oils, in particular eugenol, isoeugenol or clove oil, have a high capacity to dissolve CIPC, even in cases in which the two agents are applied separately. In particular, the use of terpenes and/or terpene oils of this type, applied before or after the CIPC, allows improved distribution of the CIPC on the potatoes. The separate application of the terpene or terpene oil therefore allows improved application, and accordingly penetration and efficacy, of the CIPC. It is thus possible to achieve CIPC concentrations of greater than 50% by weight of CIPC relative to the total volume of the solution, at ambient temperature and even at temperatures as low as 0° C. The process of the present invention therefore allows limitation of the amount of formulated product to be used.

It has also been discovered that the dissolving capacity of a terpene agent is also achieved if the CIPC is in "dry" form, i.e. if the CIPC was or is subsequently applied in pure form and if it is deposited in crystal form or in solution form, and if the solvent is evaporated during application or once it has been deposited on the bulb or tuber.

On the other hand, the process according to the invention uses terpenes or terpene oils having an elevated boiling temperature, preferably greater than 230° C., even more preferably greater than 240° C. This elevated boiling temperature thus allows the thermal fogging to be carried out at a higher temperature, providing an improved spray mist and therefore improved distribution on the treated bulbs and/or tubers. Also, the terpene compound or the oil does not decompose, or only decomposes slightly, and/or forms a high-quality mist during the thermal fogging, thus allowing improved distribution on the treated tuber.

Moreover, these elevated boiling points thus allow the risk of flammability to be reduced relative to the conventional solvents that are generally used in CIPC formulations, in which the solvents would be completely vaporised.

The terpenes and/or terpene oils exhibit suitable biocide activity against the fungi and bacteria that attack potatoes. They therefore allow the properties of the CIPC formulations to be improved.

Finally, the use of said terpenes and/or terpene oils, before or after the CIPC, maximises the anti-germination effect of the CIPC formulations.

SUMMARY OF THE INVENTION

According to a first subject, the present invention relates to a process for the anti-germination and/or biocide treatment of bulbs or tubers, especially potatoes, involving the successive application of CIPC and a terpene or terpene oil, or vice versa. Preferably, the ratio of the amount of CIPC/terpene or terpene oil is between 0.5 and 3, more preferably from more than 1 to 3, and even more preferably between 1.5 and 2.5.

According to another preferred aspect, the CIPC and the oil or the terpene may be applied in solution form. Generally the CIPC is applied in 10 to 100%, preferably 20 to 50% solution form. According to a particular aspect of the present invention, the CIPC is applied in pure form. Said solutions may contain one or more emulsifiers, more preferably a non-ionic emulsifier. Generally, said solutions contain from 0 to 20% by weight of emulsifier.

Above and below, the percentages given are by weight/volume relative to the total volume of the composition.

According to another subject, the present invention also relates to the use of a terpene and/or terpene oil for solubilising the CIPC on bulbs or tubers, involving the application of the terpene and/or terpene oil before or after that of the CIPC to said bulbs or tubers.

Preferably, the terpene agent is applied after the CIPC. According to a preferred aspect, the CIPC is in the form of a residue, that is in dry form, during application of the terpene agent; this is the case, in particular, if the CIPC was applied in pure form, or in solution form and the solvent has evaporated.

Nevertheless, the CIPC may also be applied after the terpene agent. In this case, the CIPC is preferably applied before drying or evaporation of the terpene agent applied to the bulb or tuber.

In all of these cases application of the second agent takes place immediately after and up to 30 days after that of the first agent. More preferably, the second agent is applied between 1 minute and 5 days after application of the first.

According to the present invention, the term "terpene" shall be taken to mean the compounds present in the essential oils derived from vegetables, such as limonene, eucalyptol, saffrol, terpineol, eugenol, isoeugenol, and menthol, preferably saffrol, terpineol, eugenol, isoeugenol, and menthol. More particularly eugenol is preferred.

According to the invention, the term "terpene oil" shall be taken to mean the natural oils from which the terpenes are extracted. These oils include, in particular, clove oil, eucalyptus oil, common mint oil, peppermint oil and citronella oil, preferably common mint oil, peppermint oil and clove oil. More particularly, clove oil is preferred.

The terpenes according to the invention also include the terpene salts and/or mixtures thereof. Particularly preferred salts include, in particular, the alkali metal salts, such as the sodium salts, the lithium salts and the potassium salts.

According to a particularly preferred embodiment, the terpene is in the form of salt or a dietarily acceptable mixture of salts. In this case, a lower volatility of the terpene is observed. The protection period of the tubers and bulbs after application of the solution according to the invention is thus extended.

The term "terpene agent" shall refer to said terpene, oil or the salts thereof.

The term "agent according to the invention" shall refer to the CIPC and to the terpene agent.

According to the present invention, the term "emulsifier" shall be taken to mean any type of agent that is conventionally used for this purpose, such as the ethoxylated fatty alcohols, the ethoxylated fatty acids, the ethoxylated alkylphenols or any other non-ionic product.

The agents according to the invention may be applied to the tubers and bulbs using any one of the methods known from the art, in particular by brushing, immersion, sprinkling, spraying, showering or thermal fogging. Preferably, the agents are applied by thermal fogging at a temperature between 180 and 350° C., more preferably between 230 and 250° C. This method is known per se.

Application may be continuous or intermittent throughout the storage period.

Preferably, application is repeated in the storage chamber approximately once every two months.

One or more agents that reduce the evaporation of the active ingredient may, of course, be added to the agents according to the invention. Agents of this type are known from the art and may be selected, in particular, from the water-dispersible polyterpenes, the glycerol esters of pine resin, the gum lacs, the lecithins, the siccative oils, polyvinyl alcohol, polyvinylpyrrolidone, the alkali metal polyacrylates and Arabic gum.

The agents may also contain various surfactants that are known per se.

The final formulation of the agents may depend on the method used for its application to the bulbs and tubers, and on the nature of the treated products. It may be prepared by methods known per se.

If the agents comprise a dietarily acceptable salt, said salt may be introduced into the solutions during the preparation thereof in salt form or in neutral form. In this last case, the salt is formed in situ by the addition of a suitable base, such as an alkali metal hydroxide (sodium or potassium hydroxide).

The amounts of the agents that have to be applied to the tubers and bulbs depend substantially on the selected application method. In general, a total of 20 to 30 g, preferably from 25 to 28 g, per tonne of treated bulbs or tubers are applied over a period of 6 months. More generally, the applied amount of active ingredient is adjusted as a function of the storage period.

DESCRIPTION OF EXAMPLES OF THE INVENTION

The following examples are provided in order to illustrate the present invention in a non-limiting manner.

Example

The effectiveness of the process according to the invention in the anti-germination treatment of potato tubers was assessed in the following manner.

1. 200 g/CIPC Formulation in a Mixture of Water-Soluble Solvents, Water and Organic Wetting Agents Applications were carried out by thermal fogging of the formulation at 180° C. using an electrical device (Electrofog XEDA), with a first application 15 days to 3 weeks after the filling of the cell. For each date, tuber samples, placed in individual mesh bags, were enclosed in boxes distributed homogenously in the storage cell. On the selected date, said samples were removed from the boxes and recorded.

2. 646 g/Eugenol Solution

Applications were carried by thermal fogging at 240° C. using the Electrofog XEDA. For each recording, samples in mesh bags were placed at the centre of the boxes among the filling tubers and removed therefrom on the desired dates for the purposes of analysis.

3. Successive Application of CIPC and Eugenol

The preceding eugenol solution was applied 5 days after the preceding CIPC application, under the conditions of tests 1 and 2 respectively.

4. Untreated Control

For each recording date, untreated tubers samples were placed in kraft paper bags arranged in customised pallet boxes preserved in the VCP cell. This cell, in which the boxes were held throughout the preservation, then removed for the recordings on the desired date, was maintained at the same set temperature.

The application conditions of formulations 1, 2, 3 and 4 are summarised in Table 1 (below).

The obtained results demonstrate a very clear decrease in the number and the size of the sprouts in the case of the successive application of CIPC and eugenol compared to the application of one or other of these agents individually. The process therefore demonstrates the synergy of these agents when applied separately.

Efficacy Test After 3 Months—Applied Products and Dosages

| | | | | | | | Experimental conditions | |
|---|---|---|---|---|---|---|---|---|
| Condition | Active ingredient | Concentration | Dosage | Active ingredient dosage | Application method | Application dates | T° of the pile | Germination state |
| 1 | CIPC | 200 g/L d = 1.0 kg/l | 60 ml/t then 40 ml/t Total = 100 ml/t | 12 ppm then 8 ppm Total = 20 ppm | Thermal fogging at 180° C. | 1st treatment on 08/11 2nd treatment on 27/12 | 8.3° C. 7.6° C. | — start of white point |
| 2 | EUGENOL | 646 g/L d = 1.076 kg/l | 65 ml/t then 3 × 23 ml/t Total = 134 ml/t | 42 ppm then 15 ppm + 15 ppm + 15 ppm Total = 87 ppm | Thermal fogging at 240° C. | 1st treatment on 08/11 2nd treatment on 29/11 3rd treatment on 20/12 4th treatment on 11/01 | 8° C. 7.6° C. 7.5° C. 7.6° C. | — start of white point sprouts ≈5 mm sprouts >5 mm |
| 3 | CIPC | 200 g/L d = 1.0 kg/l | 60 ml/t then 40 ml/t Total = 100 ml/t | 12 ppm then 8 ppm Total = 20 ppm | Thermal fogging at 180° C. | 1st treatment on 08/11 2nd treatment on 21/12 | 8.2° C. 7.5° C | — start of white point |
| | EUGENOL | 1076 g/l | 8.2 ml/t then 5.2 ml/t Total = 13.4 ml/t | 8.7 ppm then 5.5 ppm Total = 14.2 ppm | Thermal fogging at 240° C. | 1st treatment on 08/11 2nd treatment on 21/12 | — | — start of white point |
| 4 | Control | — | — | — | — | — | — | — |

The results of the Nicola varieties are summarised in Table 2 (below).
Anti-Germination Efficacy After 3 Months—Nicola Variety

| Condition | >5 mm | >2 mm | Sprout weight |
|---|---|---|---|
| 1 | 5.5 b | 13.0 c | 0.5 b |
| 2 | 71.7 a | 82.4 a | 60.2 a |
| 3 | 0.9 b | 6.3 c | 0.3 b |
| 4 | 35.3 a | 62.7 a | 10.7 a |
| Significance | HS | HS | S |
| C.V. (in %) | 63.6 | 34.6 | 152.0 |

HS: highly significant;
S: significant;
C.V.: coefficient of variation

These results demonstrate that the process according to the invention provides better results than the CIPC, on the one hand, and the eugenol on the other, as well as the combined effects of these two products.

The successive application therefore displays a synergy. This effect is probably facilitated by the capacity of the eugenol to improve the penetration of the CIPC.

Comparative Example

The following results relating to the application of CIPC and carvone, individually or in combination are described in U.S. Pat. No. 5,811,372:
- a dosage of 16.6 ppm of CIPC on its own allows 21, 52 or 59% of the treated batches of potatoes suitable for sale to be obtained;
- a dosage of 16.6 ppm of carvone on its own allows 0% of the treated batches of potatoes suitable for sale to be obtained;
- the combination of equal dosages of these two agents allows approximately 55% of the treated batches of potatoes suitable for sale to be obtained.

The use of carvone with CIPC in a ratio of 1 does not therefore significantly improve the effect of CIPC on its own.

The invention claimed is:

1. A process for the anti-germination and/or biocide treatment of potatoes comprising separate application of the following agents:
   (i) CIPC, and
   (ii) eugenol or clove oil,
   in this order or vice versa,
   wherein the second agent is applied between 1 minute and 5 days after application of the first agent.

2. The process according to claim 1, wherein the ratio of (i):(ii) is between 1.5 and 3.

3. The process according to claim 1, wherein one or both of (i) the CIPC and (ii) the eugenol or clove oil are applied in solution form.

4. The process according to claim 3, wherein the solution contains one or more emulsifiers.

5. The process according to claim 3, wherein the solution contains a non-ionic emulsifier.

6. The process according to claim 5, wherein the solution contains up to 20% by weight emulsifier.

7. The process according to claim 1, wherein one or both of (i) the CIPC or (ii) the eugenol or clove oil are applied by thermal fogging.

8. The process according to claim 7, wherein application is carried out at a temperature between 180° and 350° C.

9. The process according to claim 1, for the anti-germination treatment of potatoes.

10. The process according to claim 1, wherein the CIPC is applied in pure form.

11. The process according to claim 1, wherein (ii) the eugenol or clove oil is applied after (i) the CIPC.

12. The process according to claim 1, wherein (i) the CIPC is after (ii) the eugenol or clove oil.

13. The process according to claim 1, wherein the ratio of (i):(ii) is between 1.5 and 2.5.

14. The process according to claim 1, wherein the ratio of (i):(ii) ratio is greater than 1 and less than or equal to 3.

15. The process for solubilizing the CIPC on potatoes, comprising application of the eugenol or clove oil before or after that of the CIPC to said potatoes.

* * * * *